United States Patent
Do et al.

(10) Patent No.: US 11,673,001 B2
(45) Date of Patent: *Jun. 13, 2023

(54) APPARATUS FOR CORRECTING CIRCADIAN RHYTHM AND METHOD THEREOF

(71) Applicant: Kookmin University Industry Academy Cooperation Foundation, Seoul (KR)

(72) Inventors: Young Rag Do, Seoul (KR); Ji Hye Oh, Gyeonggi-do (KR)

(73) Assignee: Kookmin University Industry Academy Cooperation Foundation, Seoul (KR)

( * ) Notice: Subject to any disclaimer, the term of this patent is extended or adjusted under 35 U.S.C. 154(b) by 120 days.

This patent is subject to a terminal disclaimer.

(21) Appl. No.: 16/511,268

(22) Filed: Jul. 15, 2019

(65) Prior Publication Data

US 2020/0016427 A1 Jan. 16, 2020

(30) Foreign Application Priority Data

Jul. 16, 2018 (KR) .................. 10-2018-0082347

(51) Int. Cl.
*A61N 5/06* (2006.01)
*A61M 21/02* (2006.01)
(Continued)

(52) U.S. Cl.
CPC .......... *A61N 5/0618* (2013.01); *A61M 21/00* (2013.01); *A61M 21/02* (2013.01); *A61B 5/4857* (2013.01);
(Continued)

(58) Field of Classification Search
CPC ...... A61M 21/00–02; A61M 2005/587; H05B 33/08; A61B 5/4836; A61B 5/4857; A61N 2005/0626; A61N 2005/0662
See application file for complete search history.

(56) References Cited

U.S. PATENT DOCUMENTS 10,213,616 B1\* 2/2019 Grimard .................. A61N 5/06
2001/0056293 A1\* 12/2001 Brainard .................. A61N 5/06
607/88

(Continued)

FOREIGN PATENT DOCUMENTS

| JP | H08-089578 A | 4/1996 |
| KR | 10-2017-0123065 A | 11/2017 |
| KR | 10-2017-0137446 A | 12/2017 |

OTHER PUBLICATIONS

Oh et al., "Healthy, natural, efficient and tunable lighting: four-package white LEDs for optimizing the circadian effect, color quality and vision performance," Light Sci. Appl., 3, e141,2014. (Year: 2014).\*

*Primary Examiner* — Thaddeus B Cox
(74) *Attorney, Agent, or Firm* — Harness, Dickey & Pierce, P.L.C.

(57) ABSTRACT

The present disclosure provides a circadian rhythm correcting apparatus including a bio-illuminance measuring part configured to measure bio-illuminance of external light, a light source configured to irradiate light of a circadian wavelength band toward a retinal ganglion cell, a light source driver configured to drive the light source by supplying power to the light source, and a controller configured to control the light source driver on the basis of the bio-illuminance measured by the bio-illuminance measuring part, to correct the circadian rhythm.

12 Claims, 5 Drawing Sheets

(51) Int. Cl.
*A61M 21/00* (2006.01)
*A61B 5/00* (2006.01)
*H05B 44/00* (2022.01)

(52) U.S. Cl.
CPC ............... *A61M 2021/0005* (2013.01); *A61M 2021/0044* (2013.01); *A61N 2005/0636* (2013.01); *H05B 44/00* (2022.01)

(56) References Cited

U.S. PATENT DOCUMENTS

| | | | | |
|---|---|---|---|---|
| 2014/0052220 A1* | 2/2014 | Pedersen | .............. | A61N 5/0618 |
| | | | | 607/88 |
| 2016/0027282 A1* | 1/2016 | Lee | ........................ | A61B 5/681 |
| | | | | 340/573.1 |
| 2016/0193478 A1* | 7/2016 | Maxik | .................... | H05B 45/31 |
| | | | | 362/231 |
| 2017/0361124 A1* | 12/2017 | Parker | .................. | A61N 5/0613 |
| 2018/0339127 A1* | 11/2018 | Van Reen | ............ | A61N 5/0618 |

* cited by examiner

APPARATUS FOR CORRECTING CIRCADIAN RHYTHM AND METHOD THEREOF

CROSS-REFERENCE TO RELATED APPLICATION

This application claims priority to and the benefit of Korean Patent Application No. 2018-0082347, filed on Jul. 16, 2018, the disclosure of which is incorporated herein by reference in its entirety.

BACKGROUND

1. Field of the Invention

The present disclosure relates to a circadian rhythm correcting apparatus and a method thereof.

2. Discussion of Related Art

Humans live in a daily cycle known as a circadian rhythm, and the circadian rhythm is most affected by light.

When the sun rises in the morning, the sky begins to brighten, and as the sun sets, the sky darkens in the evening. According to such daily changes of the sun, various organisms have also changed and adapted over a long time, and humans are also affected by the daily changes of the sun and live in a daily cycle in which, when the sun rises in the morning, the humans get up and start their day, and in the evening when the sun sets, the humans rest and sleep.

Meanwhile, when the human body receives light in an evening time period, the secretion of melatonin, one hormone that has a great effect on sleep in the human body, is suppressed, which interferes with deep sleep and disturbs the circadian rhythm, thereby increasing the probability of exposure to various diseases.

Diseases caused by disturbance of the circadian rhythm include seasonal affective disorders, sleep disorders, depression, jet lag, and health problems associated with shift work, and in order to treat these diseases, it is necessary to balance the circadian rhythm by suppressing the secretion of melatonin in a morning time period and thus helping melatonin to be easily secreted in the evening time period.

SUMMARY OF THE INVENTION

The present disclosure is directed to providing a circadian rhythm correcting apparatus capable of correcting a disturbed circadian rhythm by irradiating light having a relatively high melatonin suppression rate toward ganglion cells on the basis of bio-illuminance measured in the periphery.

The present disclosure is also directed to providing a circadian rhythm correcting apparatus capable of effectively treating and preventing seasonal affective disorders, sleep disorders, depression, jet lag, and health diseases associated with shift work, which are diseases caused by the disturbance of a circadian rhythm.

The technical problems to be solved by the present disclosure is not limited to the above-described technical problems, and other technical problems which are not described can be clearly understood by those skilled in the art to which the present disclosure pertains from the following description.

According to an aspect of the present disclosure, there is provided a circadian rhythm correcting apparatus including a bio-illuminance measuring part configured to measure bio-illuminance of external light, a light source configured to irradiate light of a circadian wavelength band toward a ganglion cell, a light source driver configured to drive the light source by supplying power to the light source, and a controller configured to control the light source driver on the basis of the bio-illuminance measured by the bio-illuminance measuring part.

The controller may compare the bio-illuminance with reference bio-illuminance and drive the light source driver when the bio-illuminance is lower than the reference bio-illuminance.

The controller may compare the bio-illuminance with reference bio-illuminance and output a control signal corresponding to a value of a difference between the bio-illuminance and the reference bio-illuminance to the light source driver.

The light source driver may adjust an application amount or time of the power supplied to the light source on the basis of the control signal.

The reference bio-illuminance may be an illuminance value required to maintain a regular circadian rhythm, and may be changed according to a circadian time.

The circadian wavelength band may be in a range of 450 nm to 550 nm, a full-width at half-maximum transmission (FWHM) of the circadian wavelength band may in a range of 80 nm to 95 nm, and the circadian wavelength band may have an area concordance rate of 80% or more with a wavelength band of the circadian sensitivity curve.

The bio-illuminance measuring part may measure the bio-illuminance using a circadian lambda filter that passes the external light according to a circadian sensitivity curve, and the circadian sensitivity curve may be a light sensitivity characteristic curve for a hormone that controls a circadian rhythm and may be a curve having the maximum (value) in the circadian wavelength band.

The hormone that controls the circadian rhythm may be melatonin.

The bio-illuminance measuring part may measure illuminance of the external light and calculates the bio-illuminance by multiplying the measured illuminance by a circadian action factor.

The light source may irradiate the light of the circadian wavelength band toward the ganglion cell such that a melatonin suppression rate in an activity time zone becomes 80% or more.

The light source may irradiate the light of the circadian wavelength band toward the ganglion cell such that a circadian action factor is 0.8 or more, and the bio-illuminance is in a range of 350 blx to 1500 blx, in an activity time zone.

The light source may irradiate one light among light mixed with a blue wavelength band and a cyan wavelength band, light in the cyan wavelength band, and light in a white wavelength band having a color temperature ranging from 10000 K to 18000 K toward the ganglion cell.

The circadian illuminance correcting apparatus may further include an alarm part configured to provide an alarm so that a user may escape an environment in which melatonin secretion is suppressed when the bio-illuminance is equal to or greater than reference bio-illuminance.

According to another aspect of the present disclosure, there is provided a circadian rhythm correcting method including measuring bio-illuminance of external light, outputting a control signal on the basis of the measured bio-illuminance, driving a light source by supplying power to the light source on the basis of the control signal, and irradiating light of a circadian wavelength band toward a ganglion cell by the light source.

The operation of outputting the control signal may include operations of comparing the bio-illuminance with reference bio-illuminance and outputting the control signal when the bio-illuminance is lower than the reference bio-illuminance.

The operation of outputting the control signal may include an operation of outputting the control signal corresponding to a difference value between the bio-illuminance and reference bio-illuminance by comparing the bio-illuminance with the reference bio-illuminance.

The operation of driving the light source may include an operation of adjusting an amount or application time of the power supplied to the light source on the basis of the control signal.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXAMPLE EMBODIMENTS

Exemplary embodiments of the present disclosure will be described in detail below with reference to the accompanying drawings. The same reference numerals are used for the same or similar elements regardless of the drawing number, and a redundant description thereof is omitted.

In the description of the present disclosure, if it is determined that a detailed description of commonly-used technologies or structures related to the disclosure may obscure the subject matter of the present disclosure, the detailed description is omitted. Further, the attached drawings are provided to easily understand the spirit of the present disclosure, and it should not be interpreted that the spirit of the present disclosure is limited by the attached drawings.

Figure 1:
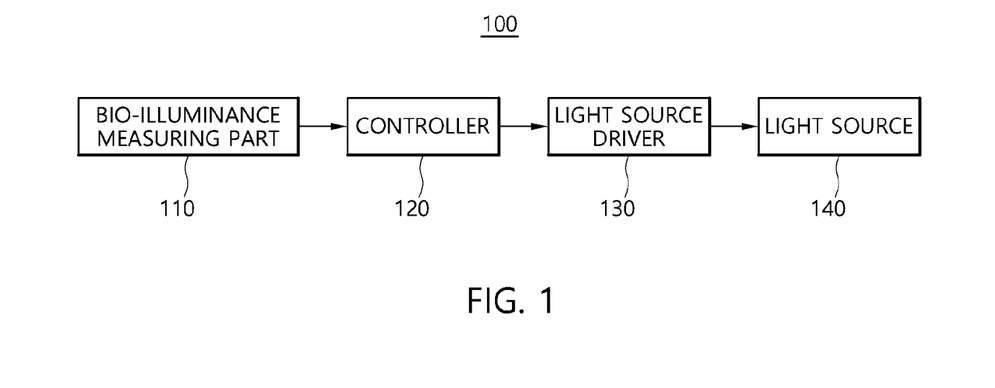
FIG. 1 is a schematic block diagram of a circadian rhythm correcting apparatus according to an embodiment of the present disclosure.
Figure 2:
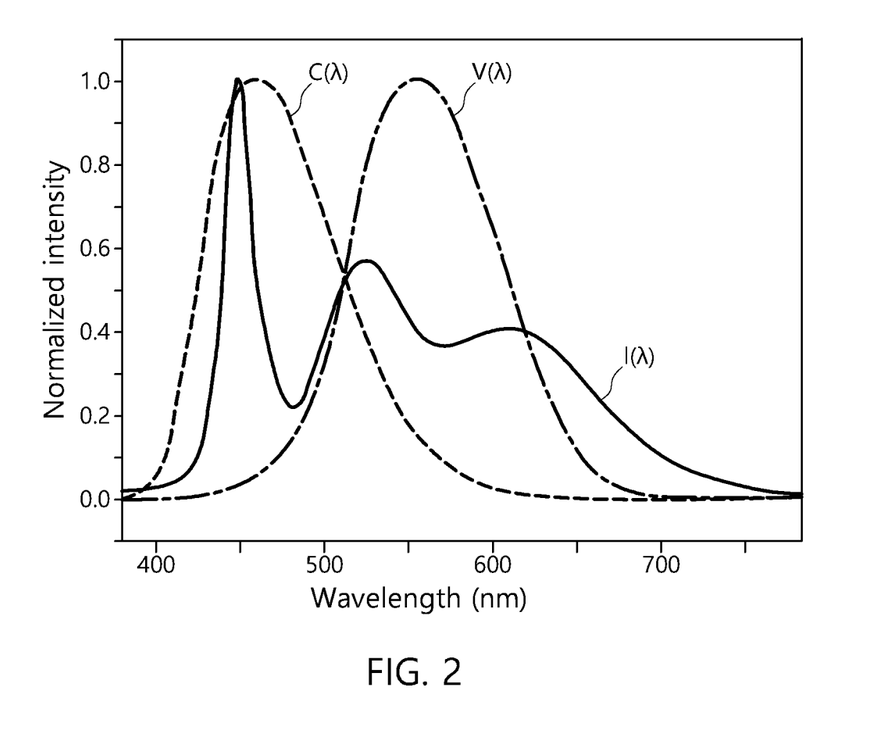
FIG. 2 is a graph illustrating a circadian sensitivity curve, a visual sensitivity curve, and a spectral curve of any light source.

FIG. 1 is a schematic block diagram of a circadian rhythm correcting apparatus according to an embodiment of the present disclosure, and FIG. 2 is a graph illustrating a circadian sensitivity curve, a visual sensitivity curve, and a spectral curve of any light source.

As shown in FIG. 1, a circadian rhythm correcting apparatus 100 according to the embodiment of the present disclosure may include a bio-illuminance measuring part 110, a controller 120, a light source driver 130, and a light source 140.

The bio-illuminance measuring part 110 may measure visual illuminance (lx) (hereinafter referred to as illuminance) of the external light using a visual illuminometer, and calculate bio-illuminance (blx) by multiplying the measured illuminance by a circadian action factor (CAF).

Here, the illuminance (lx) means the intensity of light that may be recognized by human eyes.

Meanwhile, the visual illuminometer is an element for detecting illuminance of light emitted from an external light source, and may employ various types of illuminometers known in the art.

The visual illuminometer measures the illuminance (lux) of the external light using a visual lambda filter (V($\lambda$) filter) that follows a visual sensitivity curve (visual lambda: V($\lambda$), see FIG. 2), that is, a light sensitivity characteristic curve for human eyes.

According to such a visual sensitivity curve (V($\lambda$)), the visual sensitivity curve (V($\lambda$)) has the maximum sensitivity in light having a wavelength band of about 530 nm to 580 nm (here, a main peak wavelength is 550 nm).

Meanwhile, in the visual illuminometer following the visual sensitivity curve (V($\lambda$)), different external light may have different bio-illuminance (biolux) values according to the type of external light source even though the same illuminance (lux) value is measured. This is because a luminescence spectrum varies according to the type of external light source, and when the luminescence spectrum is changed, the light sensitivity characteristic for hormones controlling the circadian rhythm changes.

Accordingly, the bio-illuminance measuring part 110 may store information, for example, a circadian action factor (CAF) or a circadian efficacy of radiation (CER) and a luminous efficacy of radiation (LER) according to the type of external light, necessary for calculating the non-visual bio-illuminance (blx) from the illuminance (lx) measured by the visual illuminometer, and the bio-illuminance measuring part 110 may calculate the bio-illuminance (blx) using the illuminance (lx) measured by the visual illuminometer and the previously stored CAF or CER and LER according to the type of external light.

The bio-illuminance (blx) may be calculated by Equation 1 below.

$$\text{Bio-illuminance (blm/m}^2\text{)}=\text{CAF (blm/lm)}\times\text{illuminance (lm/m}^2\text{)}=\text{(CER value (blm/W)/LER value (lm/W))}\times\text{illuminance (lm/m}^2\text{)} \quad \text{[Equation 1]}$$

Alternatively, the bio-illuminance measuring part 110 may also directly measure the bio-illuminance (blx) using a circadian lambda filter that passes the external light according to the circadian sensitivity curve (C($\lambda$)) (see FIG. 2).

The bio-illuminance measuring part 110 measures the bio-illuminance (biolux) using the fact that hormones such as melatonin or cortisol, which control the circadian rhythm of a human, are related to light.

Here, the circadian sensitivity curve (C($\lambda$)) is a light sensitivity characteristic curve for the hormones that control the circadian rhythm of the human, and is a curve having the maximum sensitivity in a circadian wavelength band. Here, the circadian wavelength band may be in the range of 400 nm to 550 nm, a main peak wavelength may be 460 nm, a full-width at half-maximum transmission (FWHM) may be in the range of 80 nm to 95 nm, and the circadian wavelength band may have an area concordance rate of 80% or more with a wavelength band of the circadian sensitivity curve.

Specifically, the bio-illuminance measuring part 110 uses the circadian lambda filter to measure the bio-illuminance (biolux) by passing light having the circadian wavelength band in which the light sensitivity characteristic for the hormones that control the circadian rhythm is the maximum sensitivity, that is, the light having a wavelength band of 400 nm to 550 nm, and blocking light having a wavelength band other than 400 nm to 550 nm.

Accordingly, the bio-illuminance measuring part 110 may measure the bio-illuminance (biolux) in a relatively simple manner by applying the circadian lambda filter. Further, since additional components for calculating the bio-illuminance may be omitted, the bio-illuminance measuring part 110 may be downsized, and it is possible to apply to various products at low cost.

Figure 3:
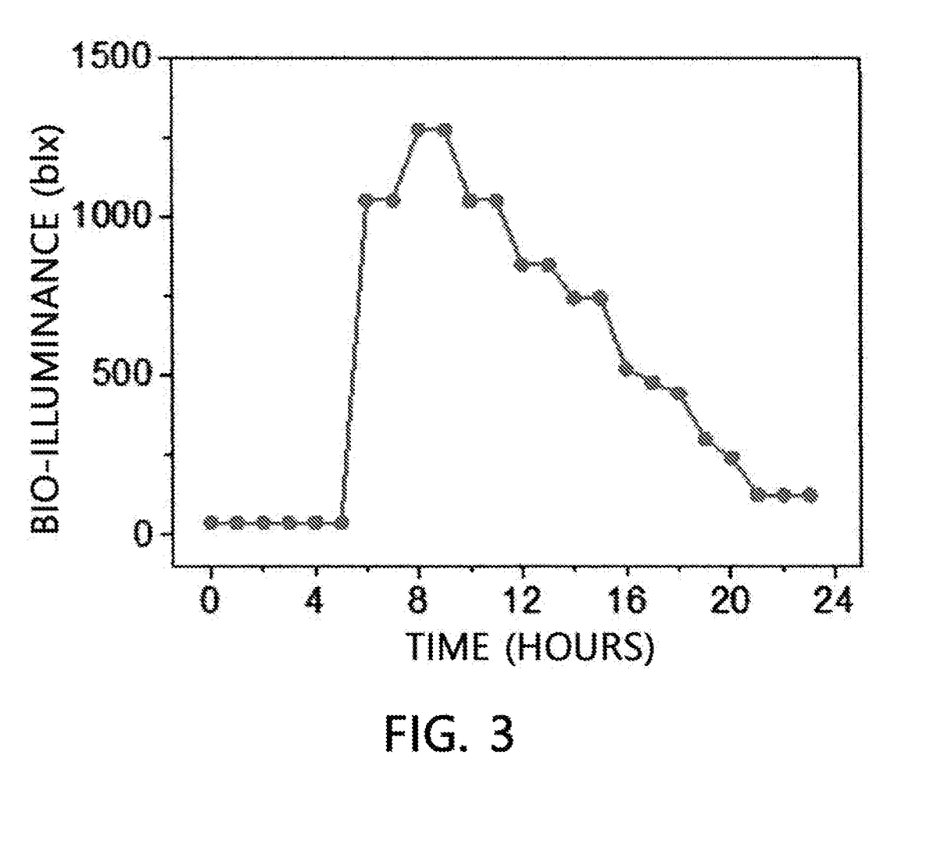
FIG. 3 is a graph illustrating reference bio-illuminance according to a circadian time.
Figure 4:
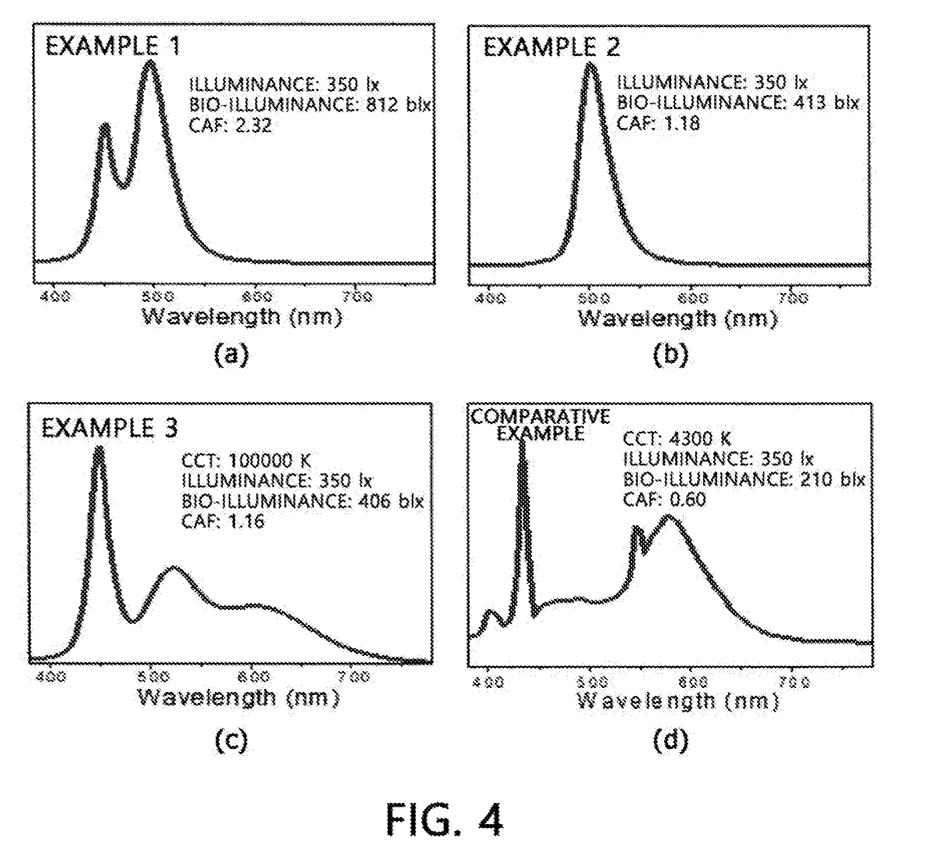
FIGS. 4A to 4D are graphs illustrating Examples and Comparative Example of light irradiated by a light source of the circadian rhythm correcting apparatus according to the embodiment of the present disclosure.

FIG. 3 is a graph illustrating reference bio-illuminance according to a circadian time.

The controller 120 may control the light source driver 130 on the basis of the bio-illuminance (blx) measured by the bio-illuminance measuring part 110.

Specifically, the controller 120 may compare the bio-illuminance (blx) with the reference bio-illuminance, and drive the light source driver 130 when the bio-illuminance is lower than the reference bio-illuminance.

Further, the controller 120 may compare the bio-illuminance (blx) with the reference bio-illuminance, and output a control signal corresponding to a value of the difference between the bio-illuminance (blx) and the reference bio-illuminance to the light source driver 130.

Here, the reference bio-illuminance is an illuminance value required to maintain a regular circadian rhythm, and varies according to the circadian time.

Specifically, as shown in FIG. 3, the reference bio-illuminance has the lowest value from 20:00 to 5:00, then increases rapidly from 5:00 to 10:00, and has the highest value at 10:00. Thereafter, the reference bio-illuminance gradually decreases from 10:00 to 23:00 and has the lowest value at 24:00.

This means that the bio-illuminance is low from 23:00 to 5:00 as it is a sleeping time zone, the bio-illuminance is relatively high from 5:00 to 20:00 as it is an activity time zone, and the bio-illuminance is maintained low from 20:00 to 23:00 as it is a preparation time for going to bed, and thus it is necessary to keep the environment having such a bio-illuminance to maintain the regular circadian rhythm.

For example, when it is determined that the bio-illuminance measured in the activity time zone is lower than the reference bio-illuminance, the circadian rhythm may be corrected by irradiating light toward ganglion cells so that the measured bio-illuminance is equal to the reference bio-illuminance.

Alternatively, without measuring the bio-illuminance, the controller 120 may maintain the balance of the circadian rhythm by driving the light source driver 130 at a certain time zone, for example, in the morning time period to suppress melatonin secretion and thus helping the melatonin secretion to occur easily in the evening time period.

The light source driver 130 is a component configured to drive the light source 140 by supplying power to the light source 140, and may receive a control signal from the controller 120 and adjust an amount or application time of the power supplied to the light source 140 on the basis of the control signal.

That is, the light source driver 130 may increase the amount or application time of the power supplied to the light source 140 as the difference value between the measured bio-illuminance and the reference bio-illuminance increases.

The light source 140 may be composed of a light emitting diode (LED) or the like, and receives the power from the light source driver 130 and irradiates light having the circadian wavelength band toward the ganglion cells. Thus, the circadian rhythm may be corrected.

Here, the ganglion cell is a type of neuron located near the inner surface (ganglion cell layer) of a human retina, and is a cell that transmits visual information from eyes to a brain. In particular, the ganglion cell does not visually sense brightness, darkness, and color, but non-visually determines the amount of light coming in, thereby affecting the adjustment of the circadian rhythm.

Figure 5:
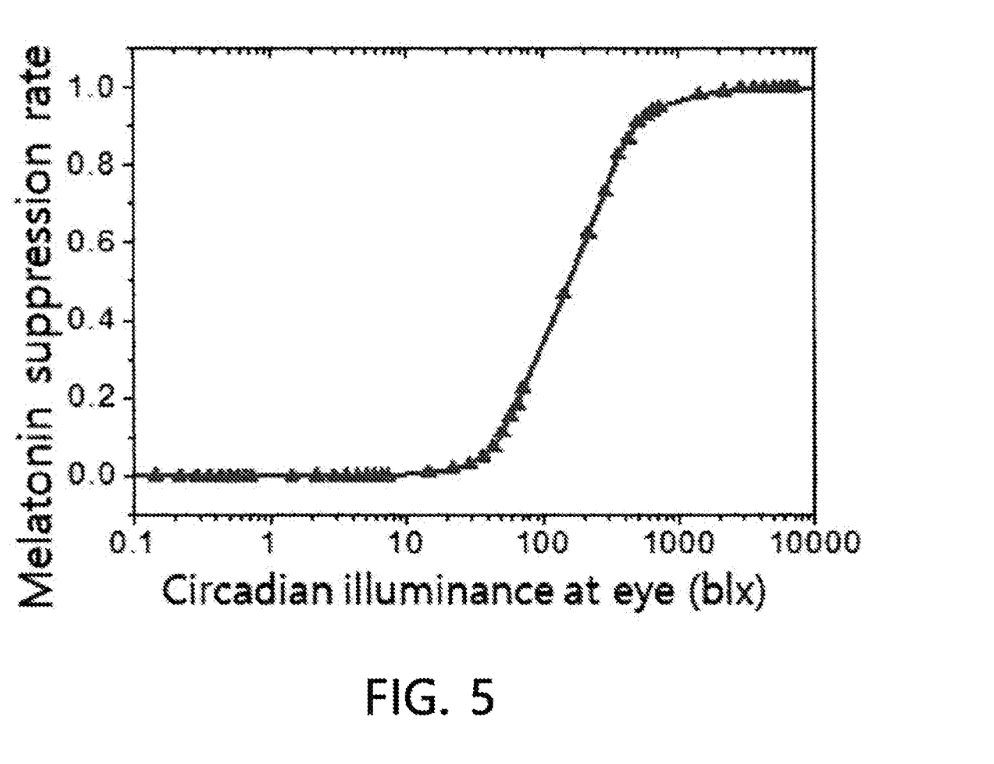
FIG. 5 is a graph illustrating a suppression rate of melatonin according to the bio-illuminance.

FIGS. 4A to 4D are graphs illustrating Examples and Comparative Example of the light irradiated by the light source of the circadian rhythm correcting apparatus according to the embodiment of the present disclosure, and FIG. 5 is a graph illustrating a suppression rate of the melatonin according to the bio-illuminance.

FIG. 4A is a graph illustrating the sensitivity of light mixed with a blue wavelength band and a cyan wavelength band, and as shown in FIG. 4A, the light mixed with the blue wavelength band and the cyan wavelength band has an illuminance of 350 lx, a bio-illuminance of 812 blx, and a CAF of 2.32.

In the case of light in which such a blue wavelength band and a cyan wavelength band are mixed, a melatonin suppression rate of 90% or more is exhibited, and it may be confirmed that the light is suitable for the circadian rhythm correction.

FIG. 4B is a graph illustrating the sensitivity of light of a cyan wavelength band, and as shown in FIG. 4B, the light of the cyan wavelength band has an illuminance of 350 lx, a bio-illuminance of 413 blx, and a CAF of 1.18.

In the case of light in such a cyan wavelength band, a melatonin suppression rate of 80% or more is exhibited, and it may be confirmed that the light is suitable for the circadian rhythm correction.

FIG. 4C is a graph illustrating the sensitivity of light in a white wavelength band having a color temperature of 10000 K, and as shown in FIG. 4C, the light in the white wavelength band with a color temperature of 10000 K has an illuminance of 350 lx, a bio-illuminance of 406 blx, and a CAF of 1.16.

In the case of light in such a white wavelength band having a color temperature of 10000 K, a melatonin suppression rate of 80% or more is exhibited, and it may be confirmed that the light is suitable for the circadian rhythm correction.

FIG. 4D is a graph illustrating the sensitivity of a fluorescent lamp having a color temperature of 4300 K, and as shown in FIG. 4D, the fluorescent lamp having a color temperature of 4300 K has an illuminance of 350 lx, a bio-illuminance of 210 blx, and a CAF of 0.60.

In the case of such a fluorescent lamp having a color temperature of 4300 K, a melatonin suppression rate of 60% is exhibited, and it may be confirmed that the light is insufficient for the circadian rhythm correction.

As shown in FIG. 5, it may be confirmed that the melatonin suppression rate is 80% at a bio-illuminance (blx) of about 350 blx, increases as the bio-illuminance (blx) increases, and is saturated at a bio-illuminance (blx) of about 1500 blx.

As described above, the light source 140 of the circadian rhythm correcting apparatus 100 according to the embodiment of the present disclosure irradiates the light of the circadian wavelength band toward the ganglion cells such that the melatonin suppression rate in the activity time zone becomes 80% or more, thereby effectively correcting the circadian rhythm.

To this end, the light source 140 of the circadian rhythm correcting apparatus 100 according to the embodiment of the present disclosure may irradiate the light of the circadian wavelength band toward the ganglion cells such that the CAF is 0.8 or more, and the bio-illuminance is in a range of 350 to 1500 blx, in the activity time zone.

Further, the light source 140 of the circadian rhythm correcting apparatus 100 according to the embodiment of the present disclosure may irradiate one of the light mixed with the blue wavelength band and the cyan wavelength band, the light in the cyan wavelength band, and the light in the white wavelength band having a color temperature ranging from 10000 K to 18000 K toward the ganglion cells.

As described above, the circadian rhythm correcting apparatus 100 according to the embodiment of the present disclosure may correct the disturbed circadian rhythm by irradiating the light having a relatively high melatonin suppression rate toward the ganglion cells on the basis of the bio-illuminance measured in the periphery.

Thus, it is possible to effectively treat and prevent seasonal affective disorders, sleep disorders, depression, jet lag, and health diseases associated with shift work, which are diseases caused by the disturbance of the circadian rhythm.

The circadian rhythm correcting apparatus 100 according to the embodiment of the present disclosure may further include an alarm part (not shown) that provides an alarm so that the user may escape the environment in which the melatonin secretion is suppressed when the bio-illuminance is equal to or greater than the reference bio-illuminance.

When the bio-illuminance measured in the evening time period is 350 blx or more, the alarm may be provided to allow the user to escape the environment in which the melatonin secretion is suppressed, so that the melatonin secretion is smoothly performed in the evening time period, thereby preventing the sleep disorders or the like.

Meanwhile, the circadian rhythm correcting apparatus 100 according to the embodiment of the present disclosure may be implemented in various forms of products that may be placed around eyes, such as glasses, patches, and the like to correct the circadian rhythm of the user.

Figure 6:
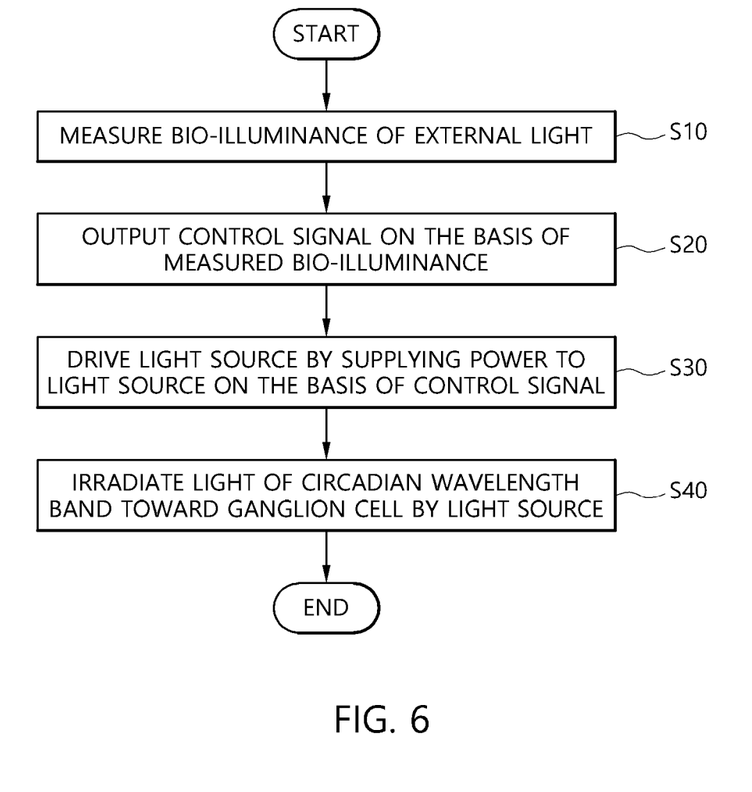
FIG. 6 is a flowchart of a circadian rhythm correcting method according to the embodiment of the present disclosure.

FIG. 6 is a flowchart illustrating a circadian rhythm correcting method according to the embodiment of the present disclosure.

Hereinafter, the circadian rhythm correcting method according to the embodiment of the present disclosure will be described with reference to FIGS. 1 to 6, but the description of the same contents as those of the circadian rhythm correcting apparatus described above will be omitted.

The circadian rhythm correcting method according to the embodiment of the present disclosure may include an operation S10 of measuring bio-illuminance of the external light, an operation S20 of outputting a control signal on the basis of the measured bio-illuminance, an operation S30 of driving a light source 140 by supplying power to the light source on the basis of the control signal, an operation S40 of irradiating light of a circadian wavelength band toward ganglion cells by the light source 140.

In operation S10 of measuring the bio-illuminance of the external light, visual illuminance (lx) (hereinafter referred to as illuminance) of the external light may be measured using a visual illuminometer, and bio-illuminance (blx) may be calculated by multiplying the measured illuminance by a CAF, or bio-illuminance (biolux) may be measured using a circadian lambda filter by passing light having a circadian wavelength band in which the light sensitivity characteristic for hormones that control circadian rhythm is the maximum sensitivity, that is, the light having a wavelength band of 400 nm to 550 nm, and blocking light having a wavelength band other than 400 nm to 550 nm.

Operation S20 of outputting the control signal may include operations of comparing the bio-illuminance with reference bio-illuminance and outputting the control signal when the bio-illuminance is lower than the reference bio-illuminance.

Operation S20 of outputting the control signal may include an operation of outputting the control signal corresponding to the difference value between the bio-illuminance and the reference bio-illuminance by comparing the bio-illuminance with the reference bio-illuminance.

Here, the reference bio-illuminance is an illuminance value required to maintain a regular circadian rhythm, and varies according to a circadian time.

In addition, operation S30 of driving the light source may include an operation of adjusting an amount or application time of the power supplied to the light source on the basis of the control signal.

Here, the amount or application time of the power supplied to the light source 140 may be increased as the difference value between the measured bio-illuminance and the reference bio-illuminance increases.

In operation S40 of irradiating the light of the circadian wavelength band toward the ganglion cells by the light source 140, the light of the circadian wavelength band is irradiated toward the ganglion cells such that a melatonin suppression rate in an activity time zone is 80% or more, thereby effectively correcting the circadian rhythm.

As described above, the circadian rhythm correcting method according to the embodiment of the present disclosure may correct the disturbed circadian rhythm by irradiating the light having a relatively high melatonin suppression rate toward the ganglion cells on the basis of the bio-illuminance measured in the periphery.

Thus, it is possible to effectively treat and prevent seasonal affective disorders, sleep disorders, depression, jet lag, and health diseases associated with shift work, which are diseases caused by the disturbance of the circadian rhythm.

According to the present disclosure, a disturbed circadian rhythm can be corrected by irradiating light having a relatively high melatonin suppression rate toward ganglion cells on the basis of bio-illuminance measured in the periphery.

Further, according to the present disclosure, it is possible to effectively treat and prevent seasonal affective disorders, sleep disorders, depression, jet lag, and health diseases associated with shift work, which are diseases caused by the disturbance of a circadian rhythm.

Effects of the present disclosure are not limited to the above-mentioned effects, and other unmentioned effects will be clearly understood by those skilled in the art from the following description.

The embodiment described in the present specification and the accompanying drawings are merely illustrative of a part of the technical ideas included in the present disclosure. Therefore, the embodiment of the present specification is not intended to limit, but is intended to illustrate the technical idea of the present disclosure, and the scope of the technical idea of the present disclosure is not limited by the embodiment. The modified examples and specific examples which could be readily inferred by a person skilled in the art within the scope of the technical ideas included in the specification and drawings of the present disclosure are to be construed as being included in the scope of the present disclosure.

What is claimed is:

1. A circadian rhythm correcting apparatus comprising:
   a bio-illuminance measurer configured to measure bio-illuminance of external light using a circadian lambda filter that passes the external light according to a circadian sensitivity curve;
   a light source configured to be disposed around a user's eyes and configured to irradiate light mixed with a blue wavelength band and a cyan wavelength band toward a ganglion cell;
   a light source driver configured to drive the light source by supplying power to the light source;
   a controller configured to control the light source driver on the basis of the bio-illuminance measured by the bio-illuminance measurer;
   the circadian sensitivity curve being a light sensitivity characteristic curve for a hormone that controls the circadian rhythm and is a curve having the maximum sensitivity in a circadian wavelength band; and
   an alarm part configured to provide an alarm so that a user may escape an environment in which melatonin secretion is suppressed when the bio-illuminance is equal to or greater than 350 blx;
   wherein the controller compares the bio-illuminance with reference bio-illuminance and outputs a control signal corresponding to a value of a difference between the bio-illuminance and the reference bio-illuminance to the light source driver, and
   wherein the reference bio-illuminance is an illuminance value required to maintain a regular circadian rhythm, and varies according to a circadian time.

2. The circadian rhythm correcting apparatus of claim 1, wherein the controller compares the bio-illuminance with reference bio-illuminance and drives the light source driver when the bio-illuminance is lower than the reference bio-illuminance.

3. The circadian rhythm correcting apparatus of claim 1, wherein the light source driver adjusts an amount or application time of the power supplied to the light source on the basis of the control signal.

4. The circadian rhythm correcting apparatus of claim 1, wherein the circadian wavelength band is in a range of 400 nm to 550 nm.

5. The circadian rhythm correcting apparatus of claim 1, wherein the hormone that controls the circadian rhythm is melatonin.

6. The circadian rhythm correcting apparatus of claim 1, wherein the bio-illuminance measurer measures illuminance of the external light and calculates the bio-illuminance by multiplying the measured illuminance by a circadian action factor.

7. The circadian rhythm correcting apparatus of claim 1, wherein the light source irradiates the light of the circadian wavelength band toward the ganglion cell such that a melatonin suppression rate in an activity time zone becomes 80% or more.

8. The circadian rhythm correcting apparatus of claim 1, wherein the light source irradiates the light of the circadian wavelength band toward the ganglion cell such that a circadian action factor is 0.8 or more, and the bio-illuminance is in a range of 350 blx to 1500 blx, in an activity time zone.

9. A circadian rhythm correcting method comprising:
   measuring bio-illuminance of external light using a circadian lambda filter that passes the external light according to a circadian sensitivity curve;
   outputting a control signal on the basis of the measured bio-illuminance;
   driving a light source by supplying power to the light source on the basis of the control signal, the light source configured to be disposed around a user's eyes;
   irradiating light from the light source toward a ganglion cell, the light mixed with a blue wavelength band and a cyan wavelength band;
   the circadian sensitivity curve being a light sensitivity characteristic curve for a hormone that controls the circadian rhythm and is a curve having the maximum sensitivity in the circadian wavelength band; and
   providing an alarm with an alarm part when the bio-illuminance is equal to or greater than 350 blx so that a user may escape an environment in which melatonin secretion is suppressed;
   wherein the operation of outputting the control signal includes an operation of outputting the control signal corresponding to a difference value between the bio-illuminance and reference bio-illuminance by comparing the bio-illuminance with the reference bio-illuminance, and
   wherein the reference bio-illuminance is an illuminance value required to maintain a regular circadian rhythm, and varies according to a circadian time.

10. The circadian rhythm correcting method of claim 9, wherein the operation of outputting the control signal includes operations of comparing the bio-illuminance with reference bio-illuminance and outputting the control signal when the bio-illuminance is lower than the reference bio-illuminance.

11. The circadian rhythm correcting method of claim 9, wherein the operation of driving the light source includes an operation of adjusting an amount or application time of the power supplied to the light source on the basis of the control signal.

12. A circadian rhythm correcting apparatus comprising:
   a bio-illuminance measurer configured to measure bio-illuminance of external light using a circadian lambda filter that passes the external light according to a circadian sensitivity curve;
   a light source configured to be disposed around a user's eyes and configured to irradiate light mixed with a blue wavelength band and a cyan wavelength band toward a ganglion cell;
   a light source driver configured to drive the light source by supplying power to the light source;
   a controller configured to control the light source driver on the basis of the bio-illuminance measured by the bio-illuminance measurer; and
   an alarm part configured to provide an alarm so that a user may escape an environment in which melatonin secretion is suppressed when the bio-illuminance is equal to or greater than 350 blx;
   wherein the controller compares the bio-illuminance with reference bio-illuminance and outputs a control signal corresponding to a value of a difference between the bio-illuminance and the reference bio-illuminance to the light source driver;
   wherein the reference bio-illuminance is an illuminance value required to maintain a regular circadian rhythm, and varies according to a circadian time; and
   the circadian sensitivity curve being a light sensitivity characteristic curve for a hormone that controls the circadian rhythm and is a curve having the maximum sensitivity in the circadian wavelength band.

* * * * *